United States Patent
Roach et al.

(10) Patent No.: US 12,408,987 B2
(45) Date of Patent: Sep. 9, 2025

(54) INSTRUMENTS FOR ROBOTIC KNEE REVISION

(71) Applicant: Orthosoft ULC, Montreal (CA)

(72) Inventors: Brian Edward Roach, Osceola, IN (US); Yann Facchinello, Prévost (CA); Daniel Moore, Blainville (CA)

(73) Assignee: Orthosoft ULC, Montreal (CA)

( * ) Notice: Subject to any disclaimer, the term of this patent is extended or adjusted under 35 U.S.C. 154(b) by 430 days.

(21) Appl. No.: 17/833,432

(22) Filed: Jun. 6, 2022

(65) Prior Publication Data

US 2022/0387121 A1 Dec. 8, 2022

Related U.S. Application Data

(60) Provisional application No. 63/197,693, filed on Jun. 7, 2021.

(51) Int. Cl.
| | |
|---|---|
| *A61B 34/20* | (2016.01) |
| *A61B 17/15* | (2006.01) |
| *A61B 34/30* | (2016.01) |
| *A61F 2/46* | (2006.01) |
| *A61B 34/10* | (2016.01) |
| *A61B 90/00* | (2016.01) |

(52) U.S. Cl.
CPC ............ *A61B 34/20* (2016.02); *A61B 17/154* (2013.01); *A61B 34/30* (2016.02); *A61F 2/461* (2013.01); *A61B 2034/102* (2016.02); *A61B 2034/2055* (2016.02); *A61B 2090/367* (2016.02); *A61B 2090/3983* (2016.02); *A61F 2002/4658* (2013.01)

(58) Field of Classification Search
CPC ..... A61B 17/80; A61B 17/8023; A61B 17/90; A61B 34/20; A61B 2034/2055; A61B 2090/3916; A61B 2090/3983; A61B 17/8061; A61F 2/461; A61F 2002/4632
See application file for complete search history.

(56) References Cited

U.S. PATENT DOCUMENTS

| | | | |
|---|---|---|---|
| 8,386,022 B2 | 2/2013 | Jutras et al. | |
| 8,571,637 B2 * | 10/2013 | Sheffer | A61B 34/20 600/407 |
| 8,814,874 B2 * | 8/2014 | Hunter | A61B 17/155 606/87 |
| 9,271,802 B2 * | 3/2016 | Neubauer | A61B 34/20 |
| 10,398,514 B2 | 9/2019 | Ryan et al. | |

(Continued)

FOREIGN PATENT DOCUMENTS

WO WO-2021127161 A1 6/2021

OTHER PUBLICATIONS

Giordano, Gerard, MD, et al., "ExactechGPS RTKA Operative Technique", Exactech, Inc. 712-32-30 Rev. A 0819, (2019), 50 pages.

*Primary Examiner* — Larry E Waggle, Jr.
(74) *Attorney, Agent, or Firm* — SCHWEGMAN LUNDBERG WOESSNER, P.A.

(57) ABSTRACT

A device for registering a bone for a robotic knee arthroplasty with a surgical robot can include a plate and a registration device. The plate can be engageable with the bone and can include a lateral portion, a medial portion, and a hinge. The registration device can be connected to the plate and can be configured to interface with the surgical robot for registration of the plate and the bone.

18 Claims, 14 Drawing Sheets

(56) References Cited

U.S. PATENT DOCUMENTS

| | | |
|---|---|---|
| 10,959,857 B2 * | 3/2021 | Wu .......................... G06T 7/246 |
| 10,987,148 B2 * | 4/2021 | Schwägli ............ A61B 17/8076 |
| 2005/0021043 A1 | 1/2005 | Jansen et al. |
| 2005/0113677 A1 * | 5/2005 | Davies ................... A61B 90/36 |
| | | 606/130 |
| 2014/0200621 A1 | 7/2014 | Malackowski et al. |
| 2021/0153918 A1 | 5/2021 | Moctezuma De La Barrera et al. |

\* cited by examiner

INSTRUMENTS FOR ROBOTIC KNEE REVISION

CLAIM OF PRIORITY

This application claims the benefit of U.S. Provisional Patent Application Ser. No. 63/197,693, filed on Jun. 7, 2021, the benefit of priority of which is claimed hereby, and which is incorporated by reference herein in its entirety

BACKGROUND

Implants are commonly used to replace various components of a human body, such as bones, bone joints, or tissues. Joint replacement procedures include shoulder replacement procedures (or shoulder arthroplasties), hip replacement procedures (or hip arthroplasties), or knee replacement procedures (knee arthroplasty). In robotic joint replacement procedures navigational systems are used to help guide a surgeon or to perform operations. During a knee arthroplasty, for example, a registration marker can be secured to a bone.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Computer-assisted surgery has been developed in order to help a surgeon to alter bones, and to position or orient implants to a desired location. Computer-assisted surgery may encompass a wide range of devices, including surgical navigation, pre-operative planning, and various robotic devices. Many conventional techniques of joint arthroplasties do not use a robot, which can result in errors or can lack precision. Robotic-assisted surgical systems can help to reduce errors and increase precision. In a robotic-assisted surgery, tracking or navigation devices can be used to help improve determination of a location of bones and instruments by the robotic surgical systems to help improve accuracy of positioning or cutting operations performed, in part or in whole, by the robotic surgical system. However, the tracking devices must be able to accommodate bones of various sizes to ensure proper fixation to the bone. Further, placement of standard pins can interfere with operations performed during a procedure, such as reaming of a tibia of femur.

This disclosure can help to address these issues by including specialized instruments that allow for standard reference arrays to be secured to bones during a robotic surgical procedure. For example, a bone plate can be securable to a femur using one or more bone screws to help limit penetration distance of the fastener to help avoid interference with reaming operations. The plate can also include a hinge to allow the plate to be adjusted to accommodate bones of various sizes. The plate can include a registration marker connected thereto so that the optical navigation tracking system can identify and locate the plate to locate the bone within space, allowing the robotic surgical system to accurately track the location of the bones during a robotic-assisted surgical procedure. The plate can also attach to the bones using screws to help limit interference between the fasteners and a reamer or stem of an implant.

The above discussion is intended to provide an overview of subject matter of the present patent application. It is not intended to provide an exclusive or exhaustive explanation of the invention. The description below is included to provide further information about the present patent application.

Figure 1:
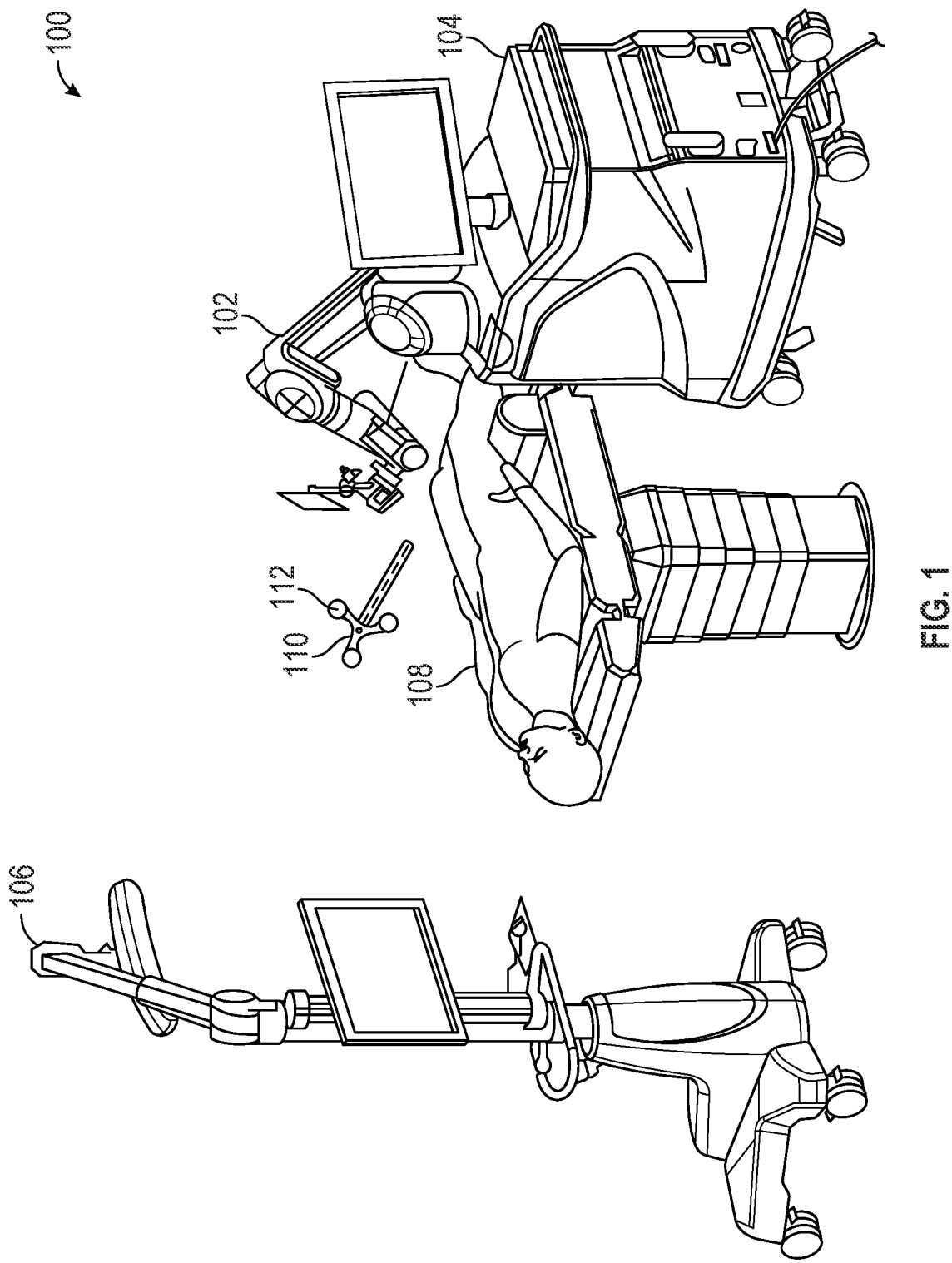
FIG. 1 illustrates a robotic surgical system including a robotic surgical device (e.g., a robot or a robotic arm) and a computer (e.g., a device having a processor).

FIG. 1 illustrates a robotic surgical system 100 including a robotic surgical device 102 (e.g., a robot or a robotic arm) and a computing device 104 (e.g., a device having a processor) in accordance with at least one example of this disclosure. In an example, the robotic surgical device 102 and the computing device 104 may be coupled, such as communicatively coupled or physically connected.

The system 100 can include an optical navigation system 106 that can detect a location of an optical navigation device 110. The optical navigation device 110 can include imaging reference points 112 recognizable (individually or in a group) by the optical navigation system 106. The system 100 is shown in relation to a patient 108. The patient 108 can be undergoing an arthroplasty procedure, for example to replace a knee joint. However, the system 100 can be used for hip or shoulder arthroplasties. The robotic surgical device 102 may be used to perform aspects of the procedure.

In an example, a bone or bones of the patient 108 may be modeled before an existing implant is removed in a revision procedure. The current bone model can be in a virtual 3D format. For example, frontal and lateral images of the bone can be used to generate a current bone model (e.g., via a front and a medial x-ray). In an example, a model of the bone can include a surface geometry of parts of the bone that are exposed. The bone modeling can include generating a 3D surface of the bone when the bone modeling is not directly performed by the imaging equipment, or if not complete. Additional structures can be modeled as well, such as cartilage, hip joint, hip, ankle, etc. A model can be generated using imaging techniques, such as from two x-rays, for example a frontal and a medial x-ray. These two x-rays may be lined up and a model may be generated using a 3D projection or estimation of the patient anatomy. Other imaging techniques may be used, such as CT scanning (computerized tomography), fluoroscopy, or like radiography methods, for example any that provide suitable resolution of images.

In an example, the patient anatomy may be modeled preoperatively, and used to plan steps of the surgical procedure. Deviations from the plan may occur during the procedure, and modifications to the plan (e.g., replanning) may occur intraoperatively, such as when using a robotic surgical device (e.g., as described above with respect to the robotic surgical device 102). A model can also be generated intraoperatively, for example using registration and optical navigation. This model may not be a fully rendered 2D or 3D model of the patient anatomy, but can instead include key points, interpolated or extrapolated points, or other information used for completing a revision procedure.

The models described with respect to the patient anatomy need not be actually rendered or displayed. Instead, the models can be used by a robotic surgical device to perform portions of a revision procedure. For example, coordinates of registered points and interpolated or extrapolated other points, simulation of coordinates as moved or cut during a procedure, or the like can be stored in memory. A robotic surgical device can retrieve data stored in the memory when performing a portion of the revision procedure.

In terms of planning, an operator may select a position or orientation of a 3D model of a replacement implant that is to be used in the arthroplasty surgery. In another example, the position or orientation may be automatically generated (e.g., using machine learning). Further planning can include determining a location for a cut plane to support the implant.

Figure 2A:
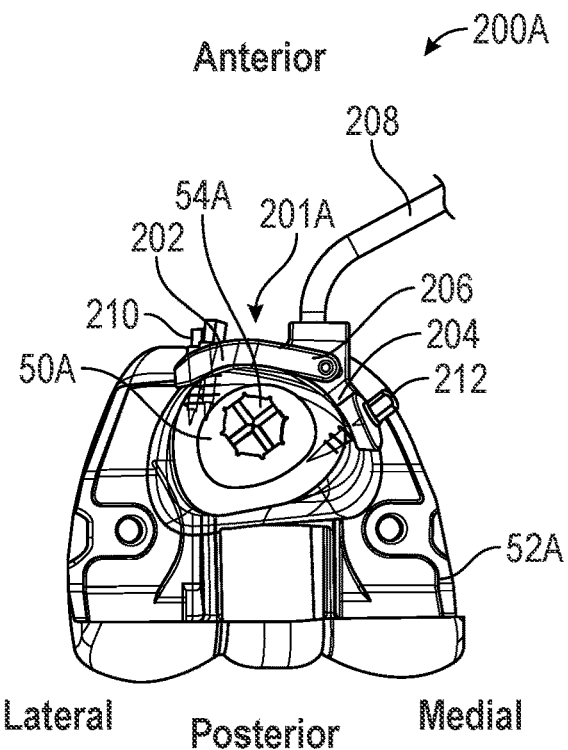
FIG. 2A illustrates a top isometric view of a femur and a portion of a registration device.
Figure 2B:
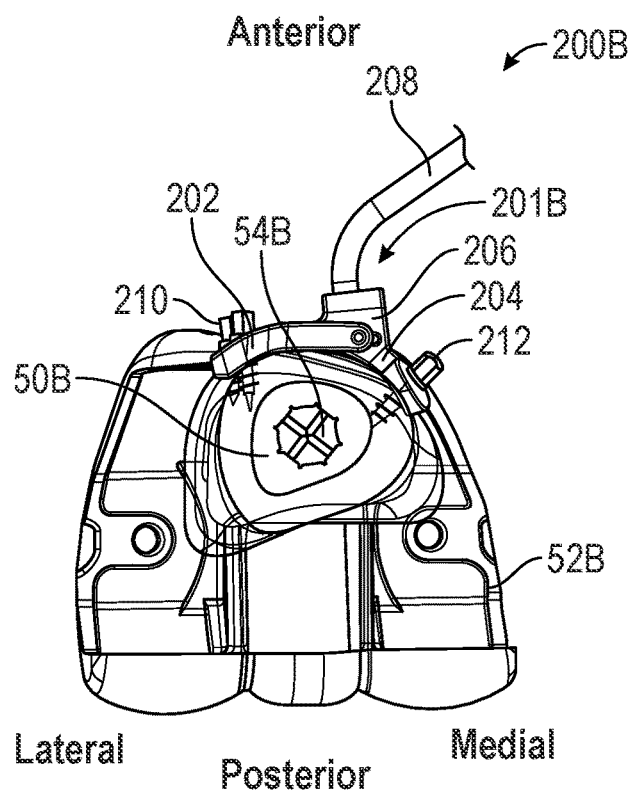
FIG. 2B illustrates a top isometric view of a femur and a portion of a registration device.
Figure 2C:
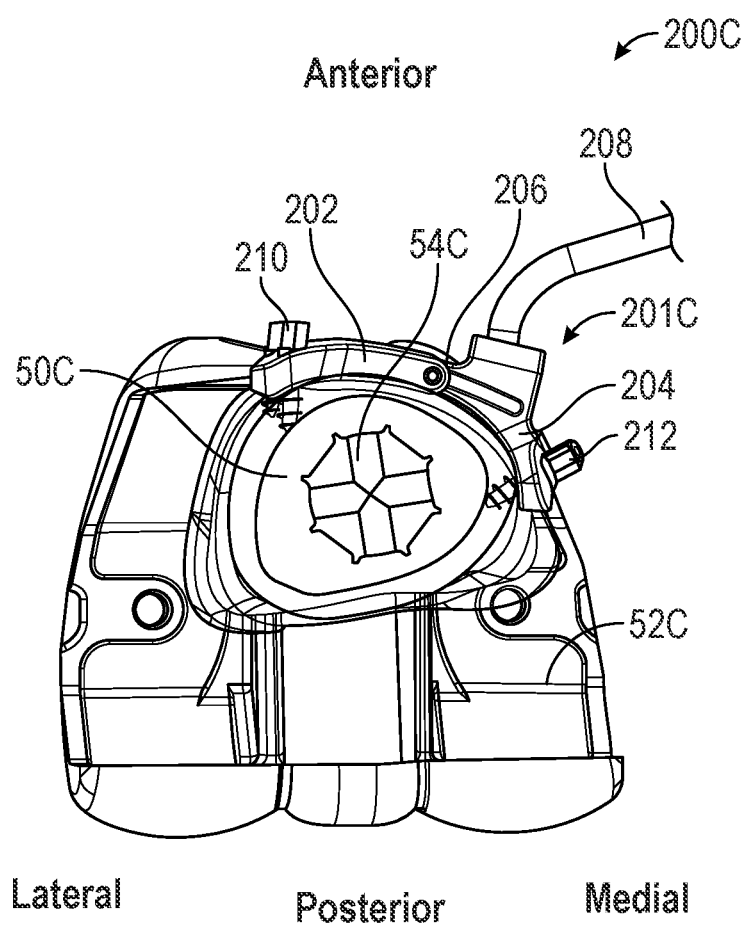
FIG. 2C illustrates a top isometric view of a femur and a portion of a registration device.

In an example, the robotic surgical device 102 can be used to cut the bone, for example using a reference guide developed from the 3D model of the bone and the existing implant. The robotic surgical device can autonomously or collaboratively with the surgeon perform the cut (e.g., using the optical navigation system 106 to guide the robotic surgical device 102). The optical navigation system 106 can track the optical navigation device 110, which can be affixed to a bone or an implant of the patient, or affixed to a portion of the robotic surgical device 102. Several optical navigation devices (e.g., trackers) 110 can be used, for example one on each of a femur, tibia, and the robotic surgical device 102. From the tracking information gathered by the optical navigation system 106 used to track each of the optical navigation devices, the robotic surgical device 102 can be guided to perform a cutting or reaming operation FIG. 2A illustrates a top isometric view of a femur 50 and a portion of a registration device 200A. FIG. 2C illustrates a top isometric view of a femur and a portion of a registration device 200B. FIG. 2C illustrates a top isometric view of a femur and a portion of a registration device 200C. FIGS. 2A-2C show how a plate of a registration device can be connected to bones of various sizes. FIGS. 2A-2C also show orientation indicators Anterior, Posterior, Lateral, and Medial. FIGS. 2A-2C are discussed together below.

A femoral implant 52 can be secured to a distal portion of the femur 50 and a portion of the stem 54 (54A, 54B, 54C) can be located within an intramedullary canal of the femur 50. The femur 50 and the implant 52 can be various sizes in FIGS. 2A-2C. For example, the femur 50A and its implant 52A can be smaller than the femur 50B and its implant 52B, which can be smaller than the femur 50C and its implant 52C. The registration devices 200A-200C of FIGS. 2A-2C can be the same device in multiple configurations and can include a plate 201 including a lateral portion 202, a medial portion, 204, and a hinge 206. The device 300 can also include a marker (or a portion of a registration marker) 208 (similar to the device 110 of FIG. 1). The registration devices 200 can also include lateral fasteners 210 and medial fasteners 212. The registration devices discussed herein can be similar to any of those shown in the patent to Sébastien Jutras, U.S. patent application Ser. No. 11/555,947, entitled "Multifaceted Tracker Device For Computer-Assisted Surgery," filed on Nov. 2, 2006, which is hereby incorporated by reference herein in its entirety.

Generally, the device 200 and its components can be made of materials such as metals, plastics, foams, elastomers, ceramics, composites, or combinations thereof. In some examples, the device 200 can be comprised of biocompatible materials such as such as stainless steels, cobalt-chromium, titanium variations, polyether ether ketone (PEEK), polyether ketone ketone (PEKK) or combinations thereof.

The lateral portion 202 and the medial portion 204 of the plate 201 can each be a plate or a portion of a plate engageable with a bone such as at a lateral portion of the femur 50 and a medial portion of the femur, respectively. The medial portion 204 of the plate 201 can be connected to the lateral portion 202. The medial portion 204 can be engageable with a bone such as at a medial portion of the femur 50. Though the lateral portion 202 and the medial portion 204 are discussed as engaging lateral and medial portions of the femur 50, the lateral portion 202 and the medial portion 204 can engage any portion of any bone. The lateral portion 202 can be connected to the medial portion 204 by the hinge 206, which can be a sliding hinge, pivoting hinge, linkage, or the like. The marker 208 can be connected to the plate 201 and can be configured to interface with the surgical robot (e.g., 102) for registration of the plate and the bone.

In operation of some examples, as shown in FIG. 2A, the lateral portion 202 can be positioned to engage an anterior or lateral portion of the femur 50A. The medial portion 204 can engage the medial portion of the femur 50A and the lateral portion 202 and the medial portion 204 can be adjusted or moved with respect to each other to position the lateral portion 202 and the medial portion 204 as desired with respect to the femur 50. Once the lateral portion 202 and the medial portion 204 are positioned as desired, the fasteners 210 can be secured through the lateral portion 202 and into the femur 50A and the fasteners 212 can be secured through the medial portion 204 and into the femur 50A. The plate 201 can thereby be secured to a small-sized femur, the femur 50A. The fasteners can be configured (e.g., sized and shaped) such that the fasteners 210 and 212 do not extend to an intramedullary canal of the femur or to the stem 54 of the implant 52, which can help limit interference between the fasteners 210 and 212 and the stem 54 (or a reamer during a reaming operation).

In operation of the example shown in FIG. 2B, the lateral plate 202 can be adjusted in position relative to the medial plate 204 via the hinge 206 to help allow the medial plate 204 to reach the medial side of the femur 50B while the lateral plate 202 can reach an anterior or lateral portion of the femur 50B. The fasteners 210 and 212 can then be used to secure the plate 201 to the femur 50B. In this way, the plate 201 can be secured to a medium-sized or average-sized femur 50B. The plate 201 can thereby be secured to a medium-sized femur, the femur 50C. Optionally, the lateral portion 202 can be contoured (e.g., sized or shaped) to engage a lateral portion of the femur 50 and the medial portion 204 can be contoured (e.g., sized or shaped to engage a medial portion of the femur 50.

In operation of the example shown in FIG. 2C, the lateral plate 202 can be adjusted in position relative to the medial plate 204 via the hinge 206 to extend as far away from each other as possible to help allow the medial plate 204 to reach the medial side of the femur 50C while the lateral plate 202 can reach an anterior or lateral portion of the femur 50C. The fasteners 210 and 212 can then be used to secure the plate 201 to the femur 50C. In this way, the plate 201 can be secured to a large-sized femur 50C. That is, the plate 201 allows for the marker 208 to be fixedly secured to femurs of various sizes with minimal adjustments to the plate 201.

Figure 3:
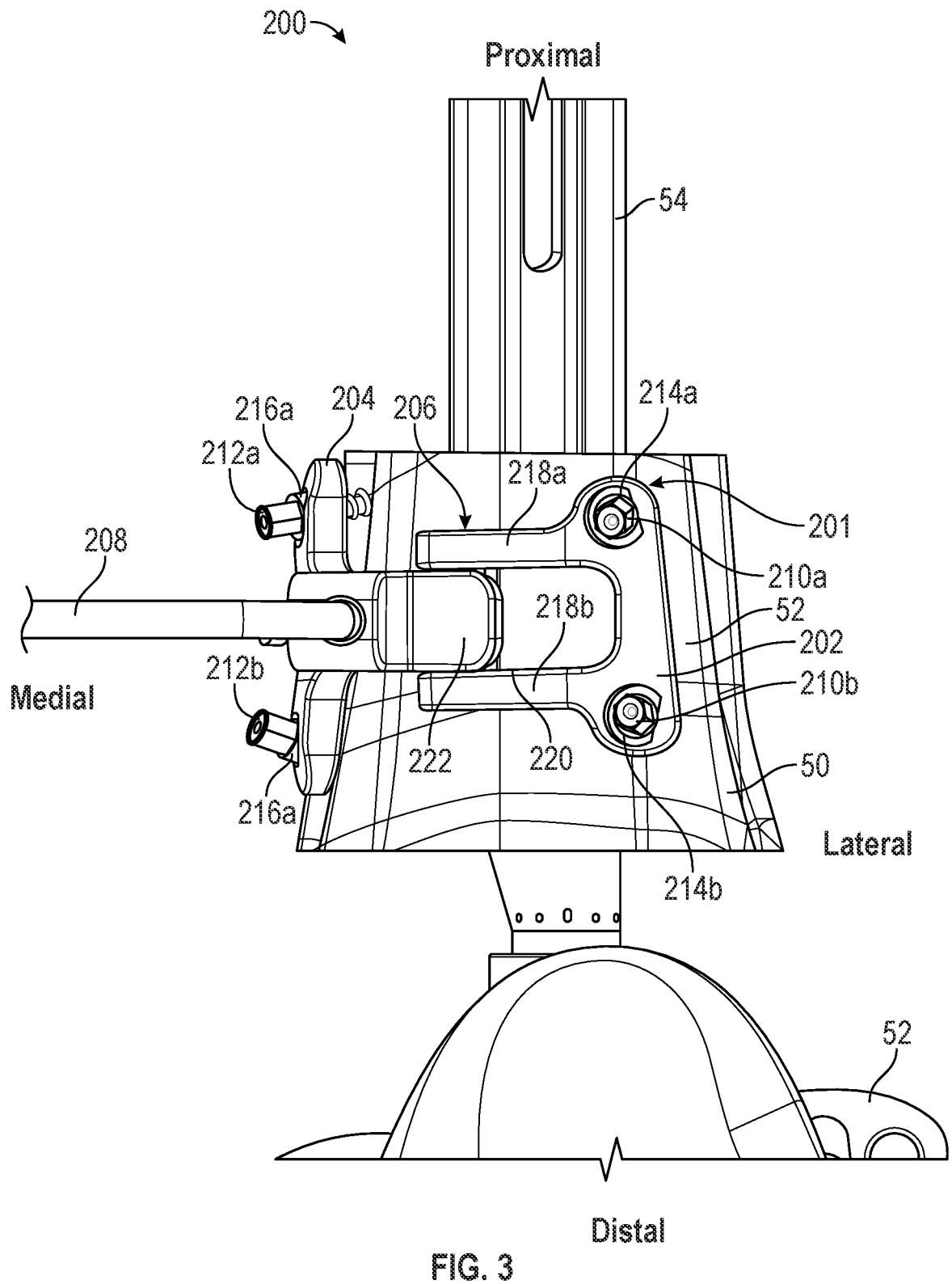
FIG. 3 illustrates a front isometric view of a femur and a portion of a registration device.

FIG. 3 illustrates a front isometric view of the femur 50 and a portion of the registration device 200. FIG. 3 also shows orientation indicators Lateral and Medial. The registration device 200 of FIG. 3 can be similar to the registration device of FIGS. 2A-2C; FIG. 3 shows additional details of the registration device.

For example, FIG. 3 shows that the lateral portion 202 can include one or more fastener bores 214a and 214b for receiving the fasteners 210a and 210b, respectively, therethrough to secure the lateral portion 202 to the femur 50. Similarly, the medial portion 204 can include one or more fastener bores 216a and 216b for receiving the fasteners 212a and 212b, respectively, therethrough to secure the medial portion 204 to the femur 50.

FIG. 3 also shows that the hinge 206 can be defined, at least in part, by a pair of arms 218a and 218b of the lateral portion 202, where the arms 218 can be relatively elongate members defining a channel or slot 220 therebetween. FIG. 3 further shows that the medial portion 204 can include a block or a slider block 222 connected to the arms 218 and located at least partially in the channel 220. The slider block 222 can be secured to the lateral portion 202 by pins (shown in FIG. 4) that allow the slider block to translate within the slot 220 to allow relative lateral-medial movement of the lateral portion 202 and the medial portion 204 with respect to each other. The hinge 206 can thereby allow for the lateral portion 202 and the medial portion 204 to be adjusted, as desired, to engage a patient's femur (or other bone).

Figure 4:
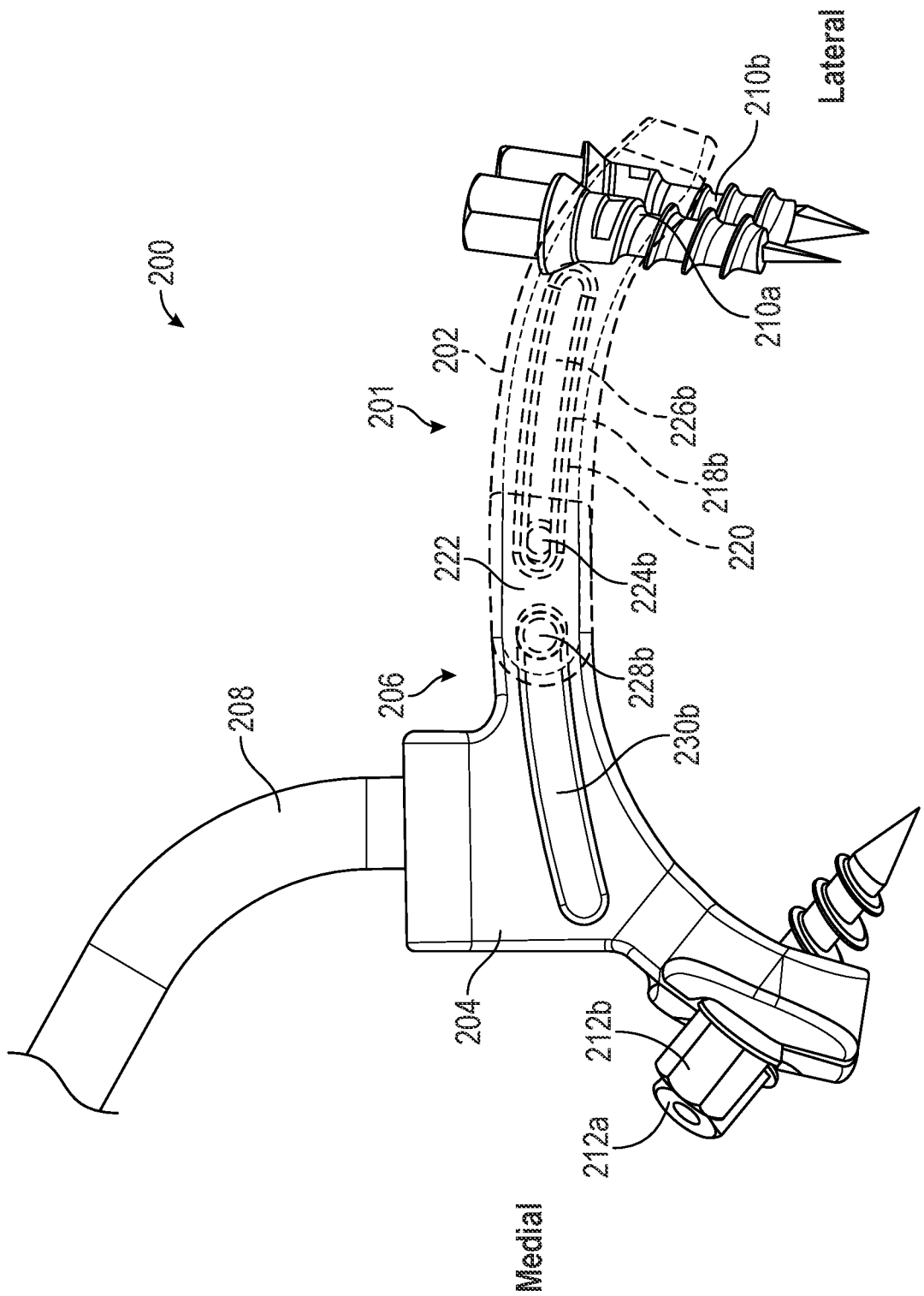
FIG. 4 illustrates top isometric view of a portion of a registration device.

FIG. 4 illustrates top isometric view of a portion of the registration device 200. FIG. 4 also shows orientation indicators Lateral and Medial. The registration device 200 of FIG. 4 can be similar to the registration device of FIGS. 2A-3; FIG. 4 shows additional details of the registration device.

For example, FIG. 4 shows a first pin 224b that can be connected to an outer portion of the slider block 222 and can be positioned in a first guide channel 226b of the arm 218b. Similarly, a second pin 224a can be connected to an outer portion of the slider block 222 (opposite the first pin 224b) and can be positioned in a second guide channel 226a of the arm 218a.

FIG. 4 also shows a third pin 228b that can be connected to an inner portion of the arm 218b and can be positioned in a third guide channel 230b of the slider block 222. Similarly, a fourth pin 228a can be connected to an inner portion of the arm 218a (opposite the third pin 228b) and can be positioned in a fourth guide channel 230a of the slider block 222.

Each of the guide channels 226 and 230 can include ends or stops engageable with the pins to help limit translation of the pins 224 and 228 and the slider block 222 and therefore the lateral portion 202 with respect to the medial plate 204. Additionally, by using multiple of the pins 224 and 228, the pins 224 and 228 can engage edges of the guide channels 226 and 230, respectively, to help limit rotation of the lateral portion 202 with respect to the medial portion 204.

Figure 5:
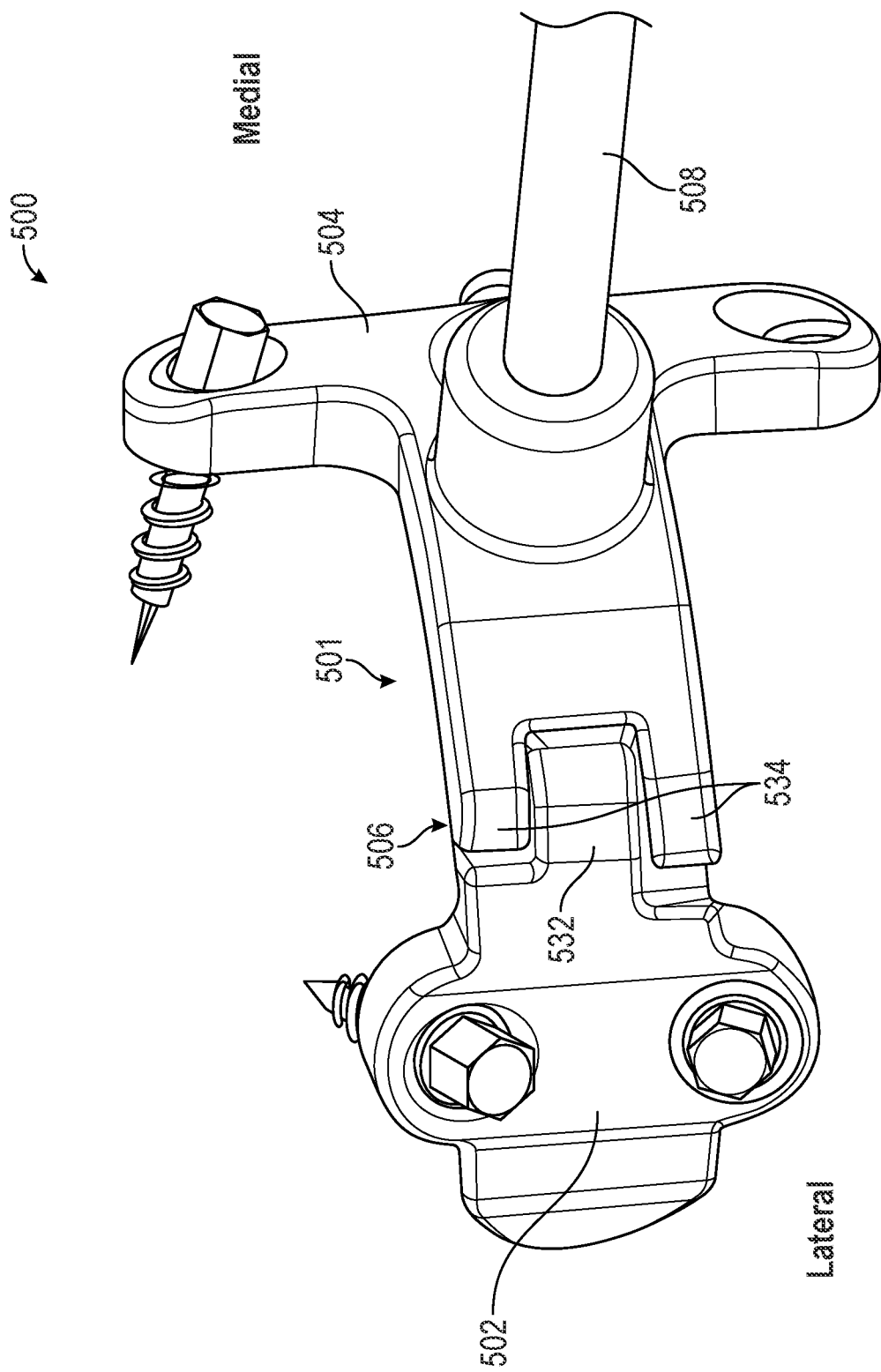
FIG. 5 illustrates front isometric view of a portion of a registration device.

FIG. 5 illustrates front isometric view of a portion of a registration device 500. FIG. 5 also shows orientation indicators Lateral and Medial. The registration device 500 can be similar to the registration device 200 discussed above; the registration device 500 can differ in that the registration device 500 can include a hinge that rotates or pivots. Any of the registration devices discussed above or below can be modified to include such a hinge.

More specifically, the registration device 500 can include a plate 501 and a marker 508. The plate 501 can include a lateral portion 502, a medial portion 504, and a hinge 506. The lateral portion 502 can be connected to the medial portion 504 by the hinge 506. The hinge 506 can be defined, at least in part, by knuckle 532 of the lateral portion 502 and knuckles 534 of the medial portion 504. A pin or fastener can extend through the knuckles to help form the joint 506.

In operation, the knuckles 534 and 532 can pivot about the pin to allow relative rotation of the knuckles 532 and 534 and therefore relative rotation of the lateral portion 502 and the medial portion 504. In this way, the lateral portion 502 and the medial portion 504 can be rotated to obtain a desired position or orientation of the lateral portion 502 and the medial portion 504 for securing of the plate 501 to a bone (e.g., a femur or tibia).

Figure 6:
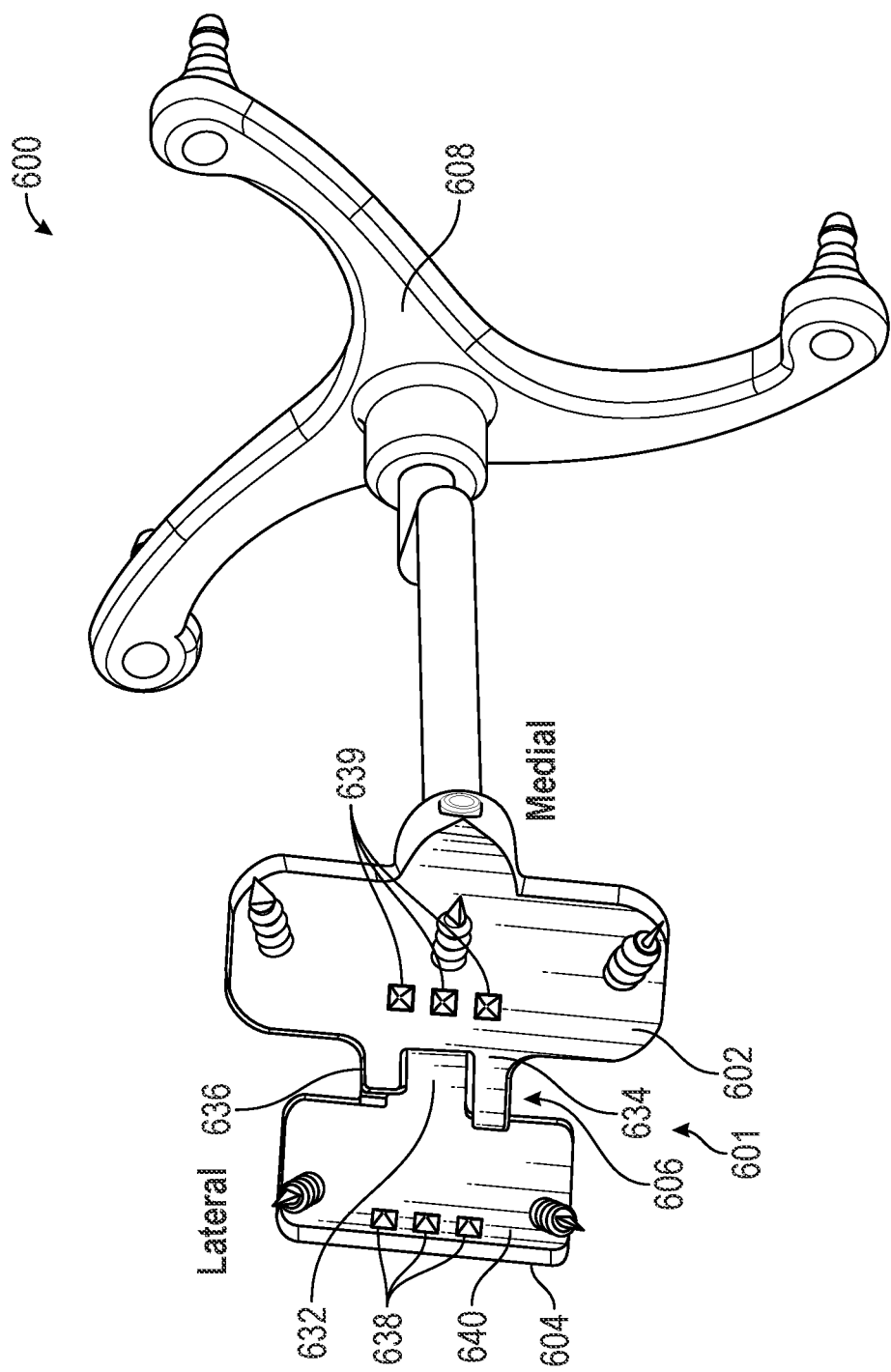
FIG. 6 illustrates front isometric view of a femur and a portion of a registration device.

FIG. 6 illustrates front isometric view of a femur and a portion of a registration device. FIG. 6 also shows orientation indicators Lateral and Medial. The registration device 600 can be similar to the registration device 500 discussed above; the registration device 600 can differ in that the registration device 600 can include bone spikes. Any of the registration devices discussed above or below can be modified to include bone spikes.

More specifically, the registration device 600 can include a plate 601 and a marker 608. The plate 601 can include a medial portion 602, a lateral portion 604, and a hinge 606. The medial portion 602 can be connected to the lateral portion 604 by the hinge 606. The hinge 606 can be defined, at least in part, by knuckle 632 of the medial portion 602 and knuckles 634 of the lateral portion 604. FIG. 4 also shows a pin 636 or fastener that can extend through the knuckles to help form the joint 606.

The lateral portion 604 can also include bone spikes or projections 638. The bone spikes 638 can extend away from an inner surface 640 (e.g., a surface configured or contoured to engage the femur 50) of the lateral portion 604. The bone spikes 638 can be configured to penetrate the bone 50 or to increase friction therebetween such as to temporarily secure the lateral portion 604 to the bone 50 before the fasteners are secured to the bone 50. Though three bone spikes are shown, the lateral portion 604 can include 1, 2, 4, 5, 6, 7, 8, 9, 10, or the like bone spikes. The medial portion 602 can also include one or more bone spikes 639.

Figure 7:
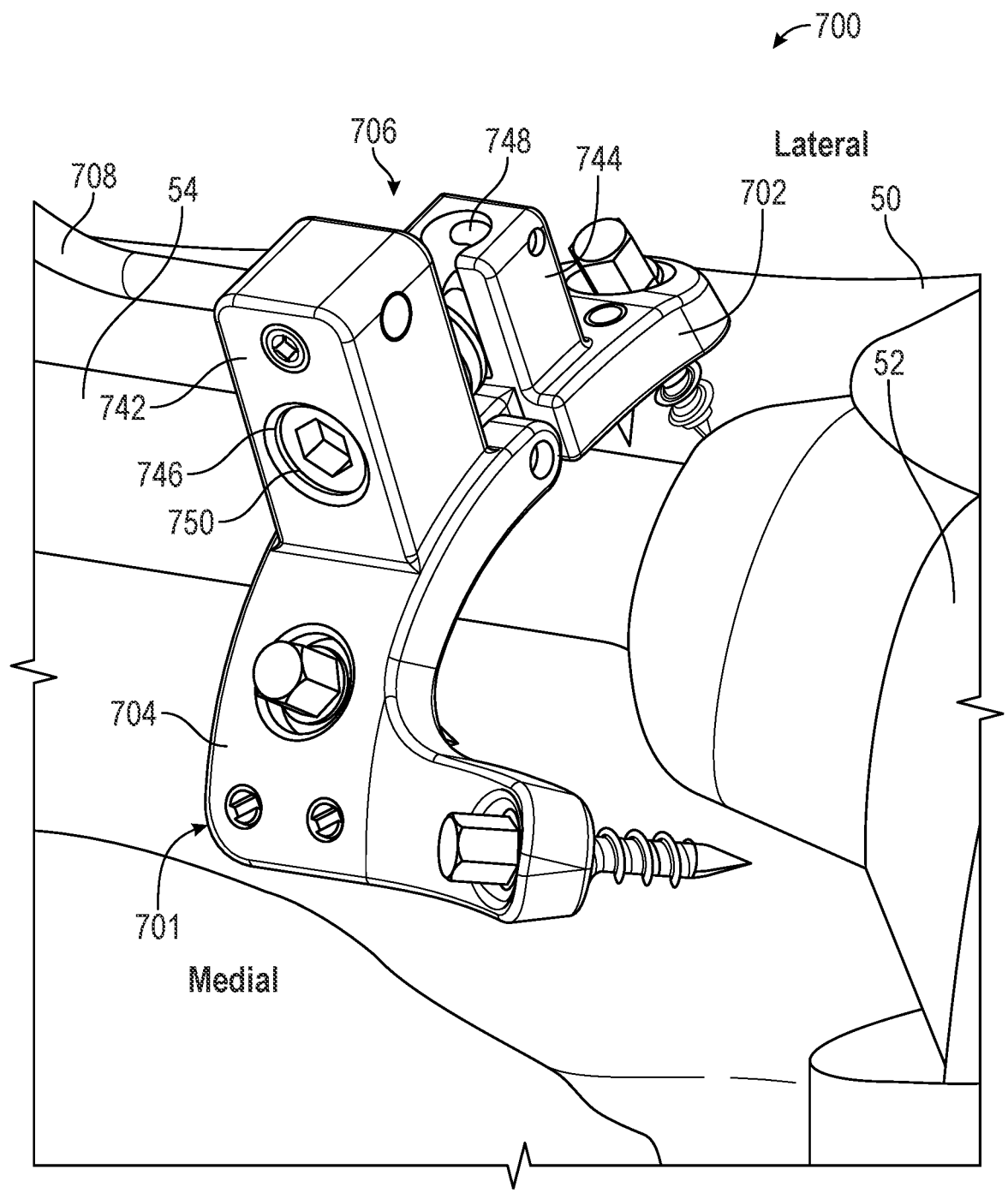
FIG. 7 illustrates front isometric view of a femur and a portion of a registration device.

FIG. 7 illustrates front isometric view of a femur 50 and a portion of a registration device 700. FIG. 7 also shows an implant 52 including a stem 54 and orientation indicators Lateral and Medial. The registration device 700 can be similar to the registration devices 200, 500, and 600 discussed above; the registration device 700 can differ in that the registration device 700 can include an adjustable translating hinge. Any of the registration devices discussed above or below can be modified to include such a hinge.

More specifically, the registration device 700 can include a plate 701 and a marker 708. The plate 701 can include a lateral portion 702, a medial portion 704, and a hinge 706.

The lateral portion 702 can be connected to the medial portion 704 by the hinge 706. The hinge 706 can be defined, at least in part, by a boss 742 of the lateral portion 702 and a boss 744 of the medial portion 704. The boss 742 can include a bore 746 and the boss 744 can include a channel 748.

The hinge 706 can also include an actuator, adjustment member, or screw 750. The adjustment member 750 can be inserted through the bore 746 and can be connected to the channel 748 to form, at least in part, the hinge 706. The adjustment member 750 can be threadably engaged with the bore 746 and can form a socket joint with the channel, such that the adjustment member 750 can be captured or captivated by the channel 748 but free to rotate with respect thereto. Such an arrangement can allow for rotation of the adjustment member 750 to cause translation of the boss 742 with respect to the boss 744 and therefore translation of the lateral portion 702 with respect to the medial portion 704, such as before securing the lateral portion 702 or medial portion 704 to the bone 50. This hinge 706 can thereby allow for fine control of the relative positions of the lateral portion 702 and the medial portion 704.

Figure 8:
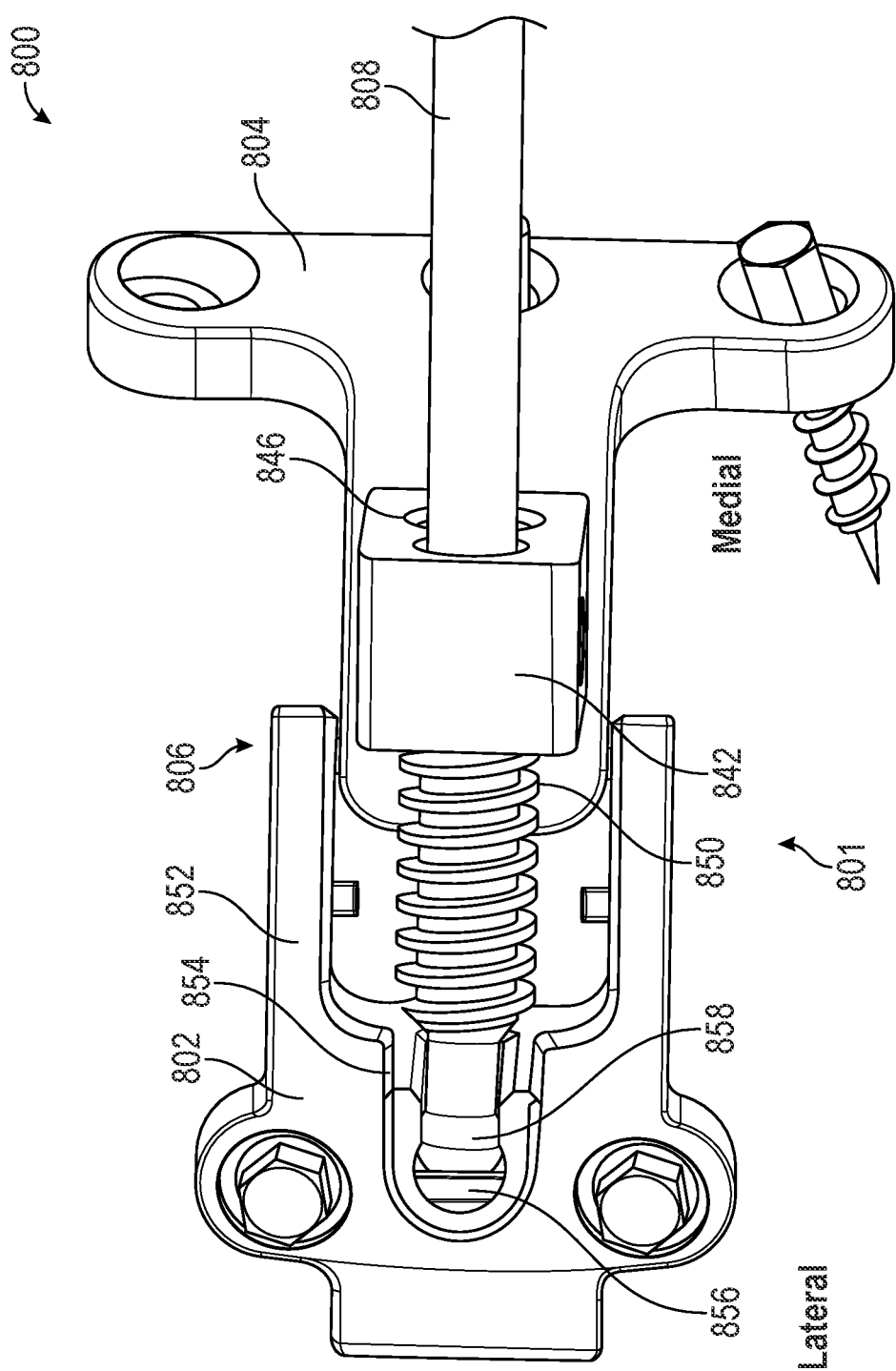
FIG. 8 illustrates front isometric view of a portion of a registration device.

FIG. 8 illustrates front isometric view of a portion of a registration device 800. FIG. 8 also shows orientation indicators Lateral and Medial. The registration device 800 can be similar to the registration device 700 discussed above. Any of the registration devices discussed above or below can be modified to include such a hinge.

The registration device 800 can include a plate 801 and a marker 808. The plate 801 can include a lateral portion 802, a medial portion 804, and a hinge 806. The lateral portion 802 can be connected to the medial portion 804 by the hinge 806. The hinge 806 can be defined, at least in part, by a boss or slider block 842 of the lateral portion 802 and a slot or channel 852 of the medial portion 804. The boss 842 can include a bore 846. The medial portion 804 can include a second channel 854 and a pin 856. The hinge can also include an actuator, adjustment member, or screw 850 including a head 858.

The adjustment member 850 can be threadably secured to the bore 846 of the slider block 842 and the head 858 can form a socket joint with the second slot 854, such that the adjustment member 850 is captured in the second slot 854 by the pin 856 such that the head is free to rotate in the second slot 854 but is limited in translation with respect to the second channel 854. The slider block 842 can be located at least in part in the channel 852 of the lateral portion 804. In operation, the adjustment member 850 can be rotated to cause translation of the medial portion 804 with respect to the lateral portion 802, such as to obtain a desired position of the lateral portion 802 with respect to the medial portion 804 before securing the lateral portion 804 or medial portion 804 to the bone 50.

Figure 9:
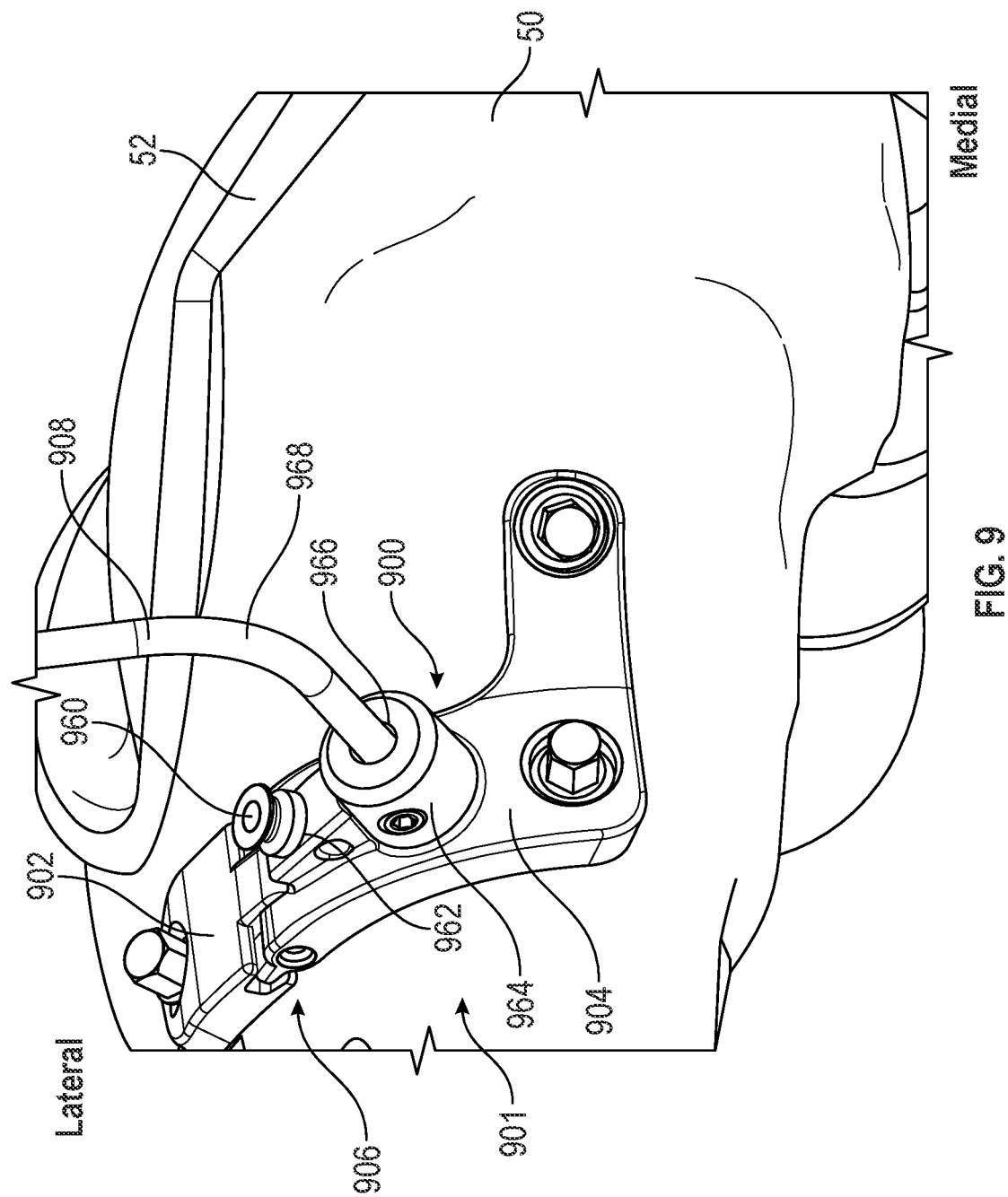
FIG. 9 illustrates front isometric view of a femur and a portion of a registration device.

FIG. 9 illustrates front isometric view of a femur 50 and a portion of a registration device 900. FIG. 9 also shows an implant 52 and orientation indicators Lateral and Medial. The registration device 900 can be similar to the registration devices 200 and 500-800 discussed above; the registration device 900 can differ in that the registration device 900 can include a bone pin. Any of the registration devices discussed above or below can be modified to include such a bone pin.

More specifically, the registration device 900 can include a plate 901 and a marker 908. The plate 901 can include a lateral portion 902, a medial portion 904, and a hinge 906. The lateral portion 902 can be connected to the medial portion 904 by the hinge 906. The hinge 906 can be similar to any of the hinges discussed herein. The plate 901 can also include a bone pin or spike 960. The bone pin 960 can be extendable through a bore 962 of the medial plate 904. In operation, a surgeon can drive the bone pin 960 through the bore and into the femur 50 to secure the medial portion 904 to the femur 50 before the fasteners of the device 900 are secured to the femur. The pin 960 can include a cap for quick extraction of the pin 960 from the bone.

FIG. 9 also shows that the device 900 can include a boss 964 extending from an outer portion of the medial portion 904 (the boss 964 can be optionally connected to the lateral portion 902). The boss 964 can define a bore 966 therein that can be configured to receive a distal portion 968 of the registration device 908 therein to secure the registration device 908 to the plate 901. Any of the previously discussed plates can be modified to include such a boss.

Figure 10:
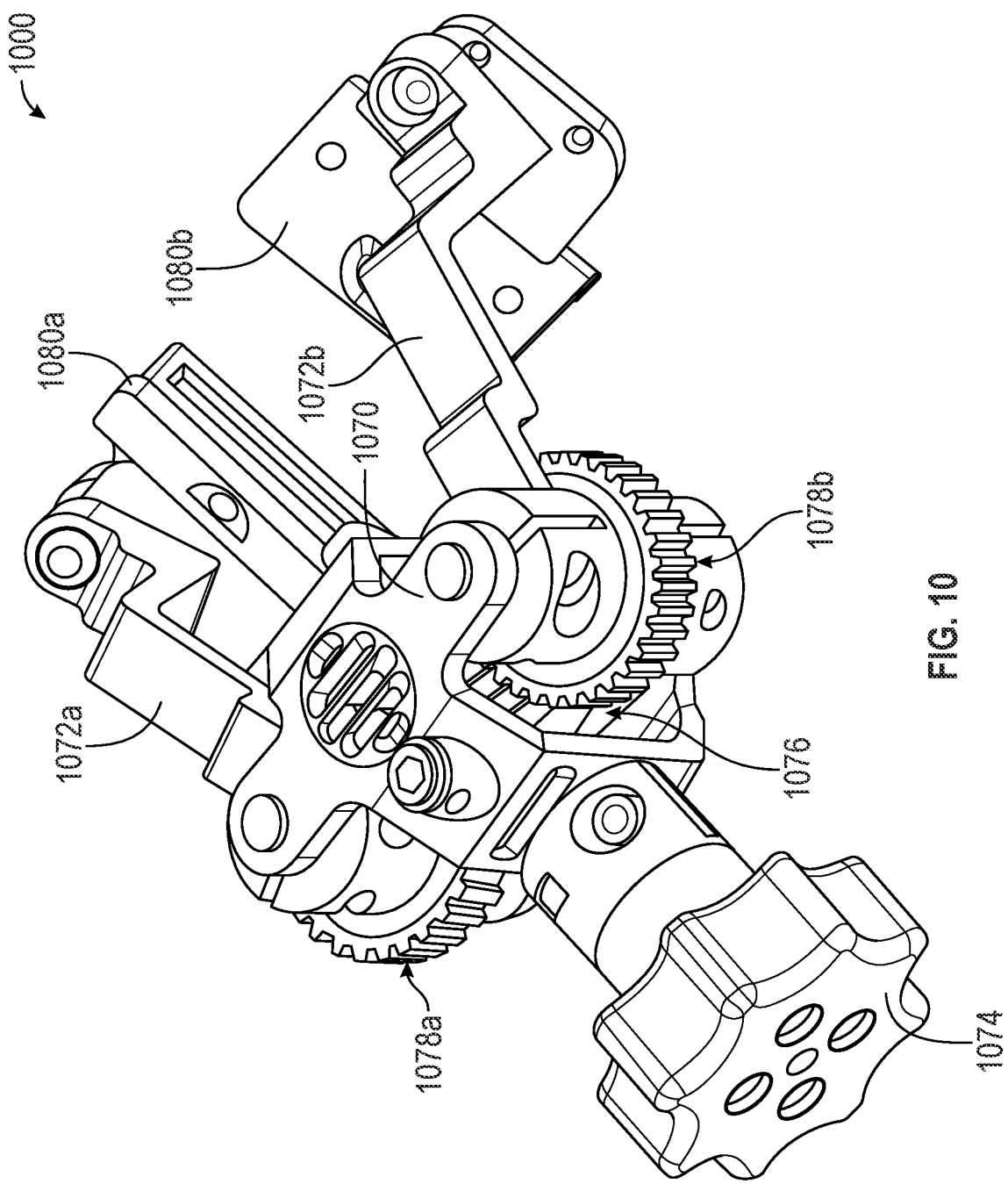
FIG. 10 illustrates front isometric view of a portion of a registration device.

FIG. 10 illustrates front isometric view of a portion of a registration device 1000. The registration device 1000 can be similar to those registration devices discussed above; the registration device 1000 can differ in that the registration device 1000 can include a clamping mechanism. Any of the registration devices discussed above or below can be modified to include such a clamping mechanism.

The registration device 1000 can include a body 1070 and arms 1072a and 1072b. The device 1000 can also include an actuator 1074, a worm drive 1076, worm gears 1078a and 1078b, and clamps 1080a and 1080b. The arms 1072a and 1072b can be connected to the clamps 1080a and 1080b, respectively. The clamps 1080 can be configured to engage bone, such as to clamp the device 1000 to bone. The actuator 1074 can be an actuator, such as a knob and can be connected to the body 1072 to allow rotation of the actuator 1074. Similarly, the worm gears 1072a and 1072b can be connected to the body 1070 but can be rotatable with respect thereto. The worm drive 1076 can be connected to the body 1070 or can be connected only to the actuator 1074.

The arms 1072a and 1072b can also be connected to the worm gears 1078a and 1078b such that movement of the worm gears 1078a and 1078b can cause movement of the arms 1072a and 1072b, respectively. The worm gears 1078a and 1078b can be engaged with a worm drive 1076 that can be connected to the actuator 1074 such that rotation of the actuator 1074 can cause rotation of the worm gears 1078a and 1078b and therefore the arms 1072a and 1072b and the clamps 1080a and 1080b.

In operation of some examples, rotation of the actuator 1074 can rotate the worm drive 1076 to rotate the worm gears 1078a and 1078b. Rotation of the worm gears 1078a and 1078b can cause rotational movement of the arms 1072a and 1072b, respectively, to move the bone clamps 1080a and 1080b, such as to clamp onto a bone for temporary securing of a navigational marker to a bone.

Figure 11:
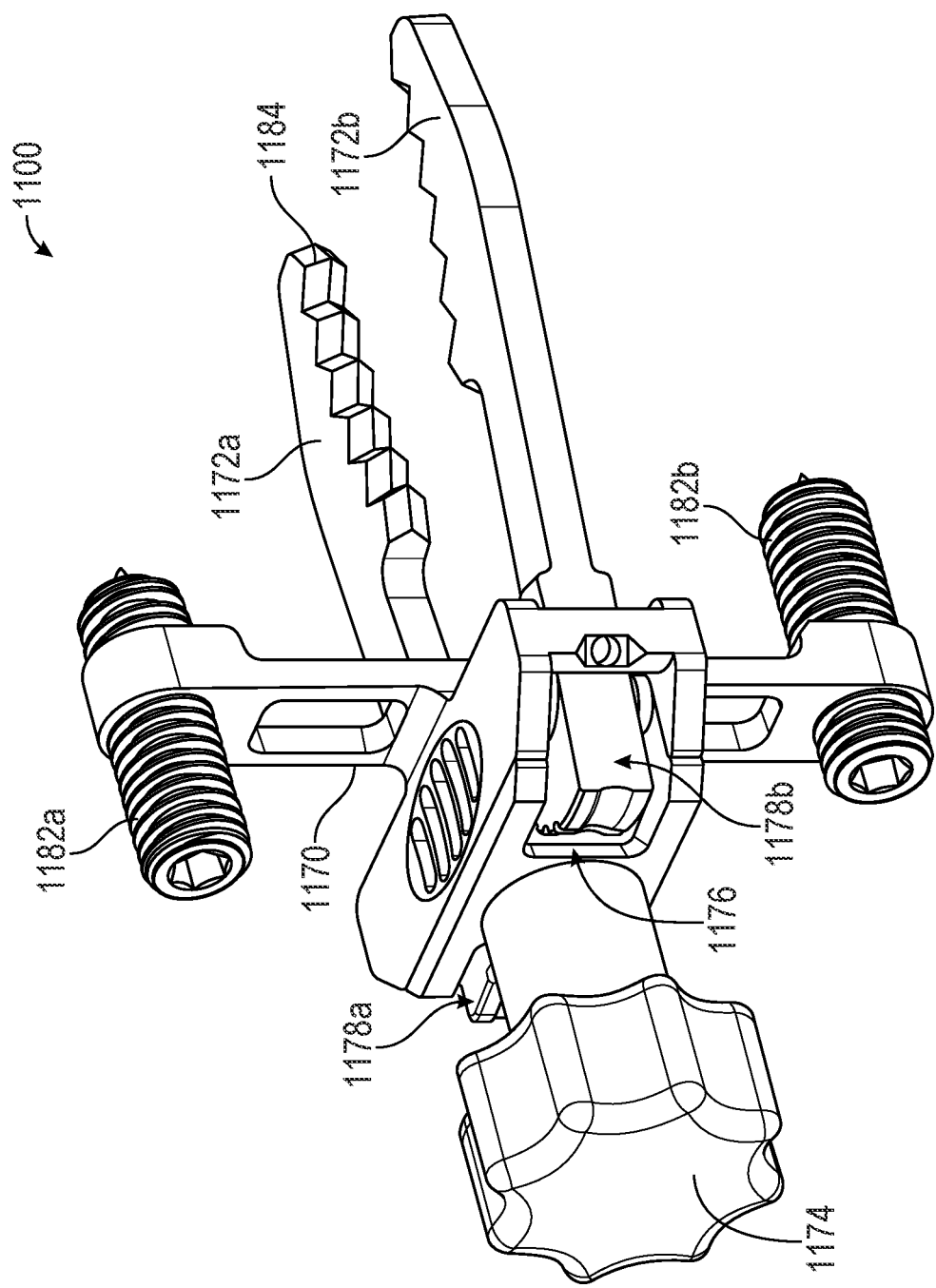
FIG. 11 illustrates front isometric view of a portion of a registration device.

FIG. 11 illustrates front isometric view of a portion of a registration device 1100. The registration device 1100 can be similar to the registration device 1000 discussed above; the registration device 1100 can differ in that the registration device 1100 can include clamping teeth and stabilizing screws. Any of the registration devices discussed above or below can be modified to include such a clamping mechanism.

The registration device 1100 can include a body 1170 and arms 1172a and 1172b. The device 1100 can also include an actuator 1174, a worm drive 1176, worm gears 1178a and 1178b, and stabilizing screws 1182a and 1182b.

Figure 12:
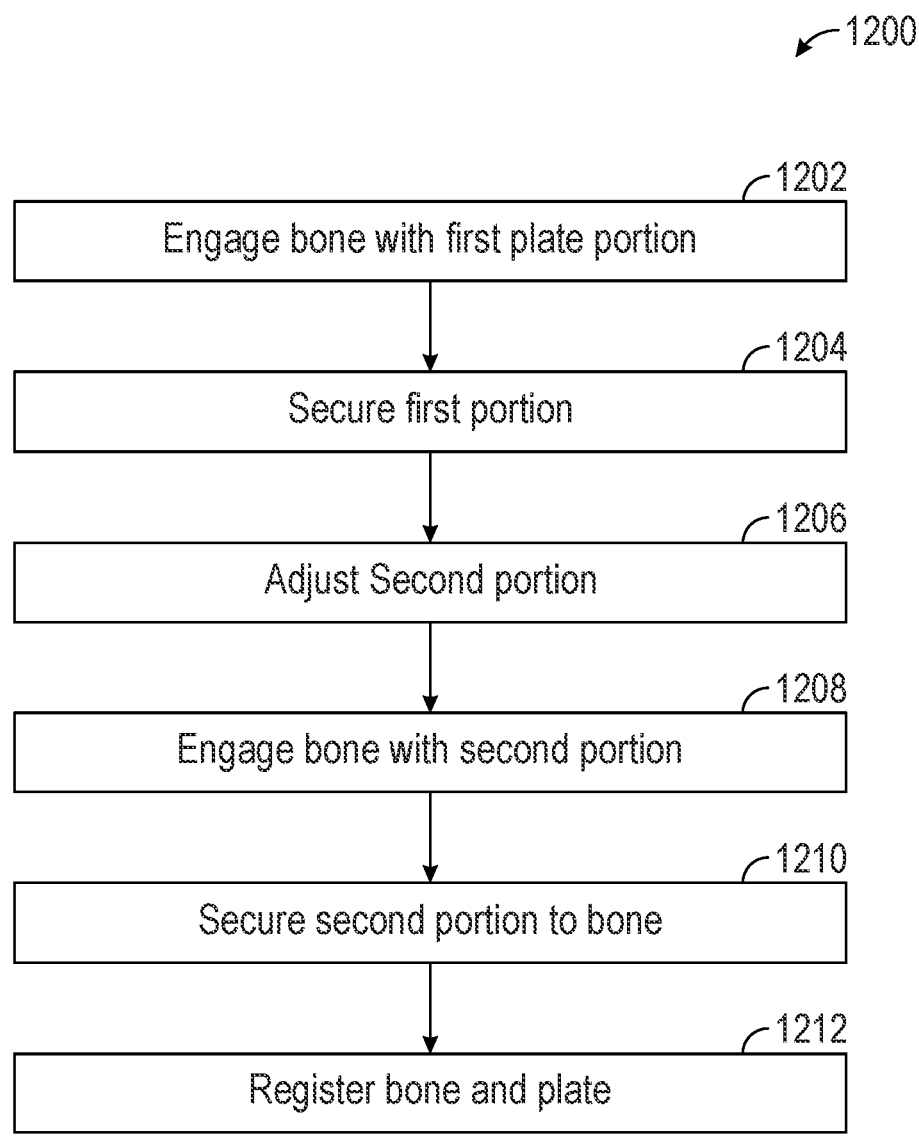
FIG. 12 illustrates block diagram of a method of using any of the devices discussed herein.

The stabilizing screws 1182a and 1182b can be connected to the body 1170 and can be threadably engaged with bores of the body 1170 such that rotation of the stabilizing screws 1182 can cause translation of the stabilizing screws 1182 with respect to the body 1170. In operation, the stabilizing screws 1182 can be operated to engage sharp points of the stabilizing screws 1182 with the bone after the arms 1172 are engaged with the bone. Such engagement of the stabilizing screws 1182 with the bone can help to limit rotational movement of the registration device 1100 with respect to the bone. The arms 1172a and 1172b can also include teeth 1184 to help increase friction between the arms 1172a and 1172b and the bone to help limit movement of the registration device 1100 with respect to the bone FIG. 12 illustrates a schematic view of the method 1200, in accordance with at least one example of this disclosure. The method 1200 can be a method of registering a bone for a robotic knee arthroplasty using a surgical robot. More specific examples of the method 1200 are discussed below. The steps or operations of the method 1200 are illustrated in a particular order for convenience and clarity; many of the discussed operations can be performed in a different sequence or in parallel without materially impacting other operations. The method 1200 as discussed includes operations performed by multiple different actors, devices, and/or systems. It is understood that subsets of the operations discussed in the method 1200 can be attributable to a single actor, device, or system could be considered a separate standalone process or method.

The method 1200 can begin at step 1202 where a bone can be engaged with a lateral (first) portion of a plate. For example, the lateral portion 202 of the plate 201 can be engaged with the femur 50. At step 1204, the lateral portion can be fastened to the bone. For example, the lateral portion 202 of the plate 201 can be fastened to the femur 50 using fasteners 210.

At step 1206, a medial portion of the plate can be adjusted using a hinge of the plate. For example, the medial portion 204 of the plate 201 can be adjusted using the hinge 206. At step 1208, engaging the bone with the medial portion of the plate. For example, the medial portion 204 of the plate 201 can be engaged with the femur 50. At step 1210, the medial portion of the plate can be fastened to the bone. For example, the medial portion 204 of the plate 201 can be fastened to the femur 50.

At step 1212, the bone and the plate can be registered using the surgical robot and a registration device secured to the plate. For example, the femur 50 and the registration marker 208 connected to the plate 201 can be registered using the robotic surgical system 100. Optionally, the bone can be registered optically using imaging reference points of the registration device using an optical navigation system associated with the surgical robot.

In some examples, the registration device can be removed from the plate. For example, the registration marker 208 can be removed from the plate before the plate 201 is secured to the femur and then the marker 208 can be later secured to the plate 201 before registration.

Optionally, the medial portion of the plate can be adjusted using the hinge, where the adjustment can include rotating the medial portion of the plate with respect to the lateral portion of the plate using the hinge. For example, the medial portion 204 of the plate 201 can be adjusted by rotating the medial portion 204 of the plate 201 with respect to the lateral portion 202 of the plate 201 using the hinge 206.

Optionally, the medial portion of the plate can be adjusted using the hinge, where the adjustment can include translating the medial portion of the plate with respect to the lateral portion of the plate using the hinge. For example, the medial portion 204 of the plate 201 can be adjusted by translating the medial portion 204 of the plate 201 with respect to the lateral portion 202 of the plate 201 using the hinge 206.

Figure 13:
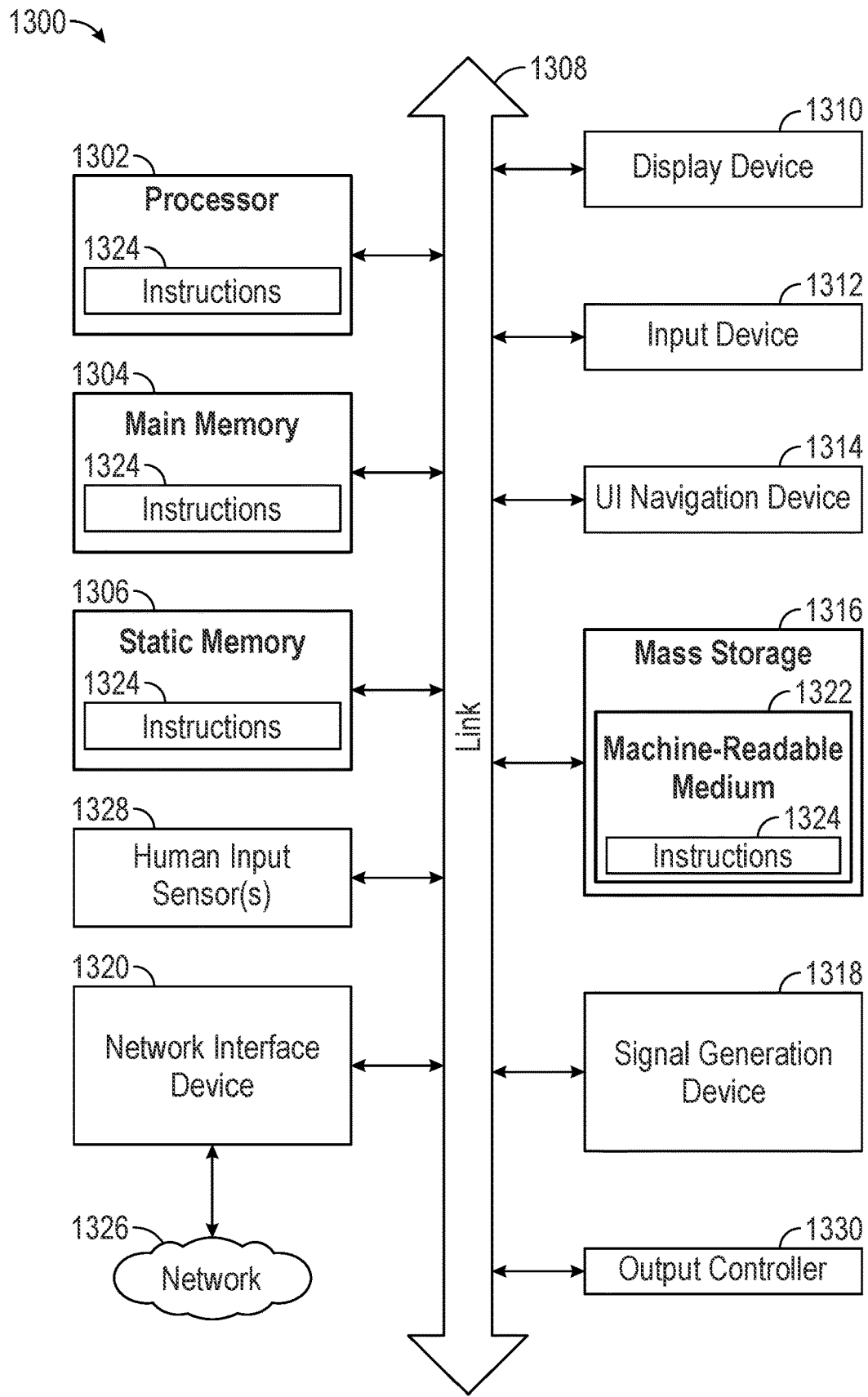
FIG. 13 is a block diagram illustrating an example of a machine upon which one or more embodiments may be implemented.

FIG. 13 illustrates a block diagram of an example machine 1300 upon which any one or more of the techniques (e.g., methodologies) discussed herein may perform. Examples, as described herein, may include, or may operate by, logic or a number of components, or mechanisms in the machine 1300. Circuitry (e.g., processing circuitry) is a collection of circuits implemented in tangible entities of the machine 1300 that include hardware (e.g., simple circuits, gates, logic, etc.). Circuitry membership may be flexible over time. Circuitries include members that may, alone or in combination, perform specified operations when operating. In an example, hardware of the circuitry may be immutably designed to carry out a specific operation (e.g., hardwired). In an example, the hardware of the circuitry may include variably connected physical components (e.g., execution units, transistors, simple circuits, etc.) including a machine readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuitry in hardware via the variable connections to carry out portions of the specific operation when in operation.

Accordingly, in an example, the machine readable medium elements are part of the circuitry or are communicatively coupled to the other components of the circuitry when the device is operating. In an example, any of the physical components may be used in more than one member of more than one circuitry. For example, under operation, execution units may be used in a first circuit of a first circuitry at one point in time and reused by a second circuit in the first circuitry, or by a third circuit in a second circuitry at a different time. Additional examples of these components with respect to the machine 1300 follow.

In alternative embodiments, the machine 1300 may operate as a standalone device or may be connected (e.g., networked) to other machines. In a networked deployment, the machine 1300 may operate in the capacity of a server machine, a client machine, or both in server-client network environments. In an example, the machine 1300 may act as a peer machine in peer-to-peer (P2P) (or other distributed) network environment. The machine 1300 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

The machine (e.g., computer system) 1300 may include a hardware processor 1302 (e.g., a central processing unit (CPU), a graphics processing unit (GPU), a hardware processor core, or any combination thereof), a main memory 1304, a static memory (e.g., memory or storage for firmware, microcode, a basic-input-output (BIOS), unified extensible firmware interface (UEFI), etc.) 1306, and mass storage 1308 (e.g., hard drive, tape drive, flash storage, or other block devices) some or all of which may communicate with each other via an interlink (e.g., bus) 1330. The machine 1300 may further include a display unit 1310, an alphanumeric input device 1312 (e.g., a keyboard), and a user interface (UI) navigation device 1314 (e.g., a mouse). In an example, the display unit 1310, input device 1312 and UI navigation device 1314 may be a touch screen display. The machine 1300 may additionally include a storage device (e.g., drive unit) 1308, a signal generation device 1318 (e.g., a speaker), a network interface device 1320, and one or more sensors 1316, such as a global positioning system (GPS) sensor, compass, accelerometer, or other sensor. The machine 1300 may include an output controller 1328, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

Registers of the processor 1302, the main memory 1304, the static memory 1306, or the mass storage 1308 may be, or include, a machine readable medium 1322 on which is stored one or more sets of data structures or instructions 1324 (e.g., software) embodying or utilized by any one or more of the techniques or functions described herein. The instructions 1324 may also reside, completely or at least partially, within any of registers of the processor 1302, the main memory 1304, the static memory 1306, or the mass storage 1308 during execution thereof by the machine 1300. In an example, one or any combination of the hardware processor 1302, the main memory 1304, the static memory 1306, or the mass storage 1308 may constitute the machine readable media 1322. While the machine readable medium 1322 is illustrated as a single medium, the term "machine readable medium" may include a single medium or multiple media (e.g., a centralized or distributed database, and/or associated caches and servers) configured to store the one or more instructions 1324.

The term "machine readable medium" may include any medium that is capable of storing, encoding, or carrying instructions for execution by the machine 1300 and that cause the machine 1300 to perform any one or more of the techniques of the present disclosure, or that is capable of storing, encoding or carrying data structures used by or associated with such instructions. Non-limiting machine readable medium examples may include solid-state memories, optical media, magnetic media, and signals (e.g., radio frequency signals, other photon based signals, sound signals, etc.). In an example, a non-transitory machine readable medium comprises a machine readable medium with a plurality of particles having invariant (e.g., rest) mass, and thus are compositions of matter. Accordingly, non-transitory machine-readable media are machine readable media that do not include transitory propagating signals. Specific examples of non-transitory machine readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 1324 may be further transmitted or received over a communications network 1326 using a transmission medium via the network interface device 1320 utilizing any one of a number of transfer protocols (e.g., frame relay, interact protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, IEEE 802.16 family of standards known as WiMax®), IEEE 802.15.4 family of standards, peer-to-peer (P2P) networks, among others. In an example, the network interface device 1320 may include one or more physical jacks (e.g., Ethernet, coaxial, or phone jacks) or one or more antennas to connect to the communications network 1326. In an example, the network interface device 1320 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 1300, and includes digital or analog communications signals or other intangible medium to facilitate communication of such software. A transmission medium is a machine readable medium.

NOTES AND EXAMPLES

The following, non-limiting examples, detail certain aspects of the present subject matter to solve the challenges and provide the benefits discussed herein, among others.

Example 1 is a device for registering a bone for a robotic knee arthroplasty with a surgical robot, the device comprising: a plate engageable with the bone, the plate comprising: a lateral portion engageable with the bone and including a lateral bore extending through the lateral portion, the lateral bore configured to receive a fastener therethrough to secure the lateral portion to the bone; a medial portion connected to the lateral portion, the medial portion engageable with the bone and including a medial bore extending through the medial portion, the medial bore configured to receive a fastener therethrough to secure the lateral portion to the bone; and a hinge connected to the lateral portion and the medial portion to allow relative movement of the lateral portion and the medial portion before the lateral portion and the medial portion are secured to the bone; and a registration device connected to the plate and configured to interface with the surgical robot for registration of the plate and the bone.

In Example 2, the subject matter of Example 1 optionally includes wherein the hinge is a pivoting hinge configured to allow the lateral portion to rotate with respect to the medial portion.

In Example 3, the subject matter of any one or more of Examples 1-2 optionally include wherein the hinge is a sliding hinge configured to allow the lateral portion to translate with respect to the medial portion.

In Example 4, the subject matter of Example 3 optionally includes wherein the sliding hinge includes a pair of pins connected to the lateral portion and the medial portion to engage the lateral portion and the medial portion to limit rotation of the lateral portion with respect to the medial portion.

In Example 5, the subject matter of any one or more of Examples 2-4 optionally include wherein the lateral portion includes a channel and wherein the medial portion includes a slider block located within the channel and translatable within the channel such that the channel guides translation of the slider block.

In Example 6, the subject matter of Example 5 optionally includes wherein the plate includes: a first pin and a second pin connected to the slider block and at least partially located in a first guide channel and a second guide channel of the lateral portion, respectively; and a third pin and a fourth pin connected to the lateral portion and at least partially located in a third guide channel and a fourth guide channel of the medial portion, respectively.

In Example 7, the subject matter of any one or more of Examples 4-6 optionally include wherein the sliding hinge includes an adjustment member connected to the lateral portion and the medial portion, the adjustment member operable to move the lateral portion with respect to the medial portion.

In Example 8, the subject matter of Example 7 optionally includes wherein the adjustment member is connected to the medial portion to form a socket joint and wherein the adjustment member forms a threaded engagement with the lateral portion.

In Example 9, the subject matter of Example 8 optionally includes wherein the hinge includes a pin detachably connected to the medial portion and engaged with an outer surface of the adjustment member to retain the adjustment member in the socket joint.

In Example 10, the subject matter of any one or more of Examples 1-9 optionally include wherein the plate include a bone engagement surface configured to engage an external bone surface.

In Example 11, the subject matter of Example 10 optionally includes wherein the bone engagement surface includes a projection engageable with the external bone surface to increase friction therebetween.

In Example 12, the subject matter of any one or more of Examples 7-11 optionally include wherein the lateral portion is contoured to engage a lateral portion of a femur and the medial portion is contoured to engage a medial portion of a femur.

In Example 13, the subject matter of any one or more of Examples 1-12 optionally include wherein the lateral portion or the medial portion includes a boss extending from an outer portion of the lateral portion or the medial portion, the boss defining a bore configured to receive a distal portion of the registration device therein.

Example 14 is a method of registering a bone for a robotic knee arthroplasty using a surgical robot, the method comprising: engaging a bone with a lateral portion of a plate; fastening the lateral portion to the bone; adjusting a medial portion of the plate using a hinge of the plate; fastening the medial portion to the bone; and registering the bone and the plate using the surgical robot and a registration device secured to the plate.

In Example 15, the subject matter of Example 14 optionally includes wherein adjusting the medial portion of the plate using the hinge includes rotating the medial portion of the plate with respect to the lateral portion of the plate using the hinge.

In Example 16, the subject matter of any one or more of Examples 14-15 optionally include wherein adjusting the medial portion of the plate using the hinge includes translating the medial portion of the plate with respect to the lateral portion of the plate using the hinge.

In Example 17, the subject matter of any one or more of Examples 14-16 optionally include wherein registering the bone includes optically imaging reference points of the registration device using an optical navigation system associated with the surgical robot.

In Example 18, the subject matter of any one or more of Examples 14-17 optionally include removing the registration device from the plate; and securing the registration device to the plate.

In Example 19, the subject matter of any one or more of Examples 14-18 optionally include engaging the bone with the medial portion of the plate.

In Example 20, the subject matter of any one or more of Examples 14-19 optionally include wherein fastening the lateral portion to the bone and fastening the medial portion to the bone include using bone screws.

In Example 21, the apparatuses or method of any one or any combination of Examples 1-20 can optionally be configured such that all elements or options recited are available to use or select from.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples or one or more aspects thereof) shown or described herein.

In the event of inconsistent usages between this document and any documents so incorporated by reference, the usage in this document controls. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The invention claimed is:

1. A device for registering a bone for a robotic knee arthroplasty with a surgical robot, the device comprising:
a plate engageable with the bone, the plate comprising:
a lateral portion engageable with the bone and including a lateral bore extending through the lateral portion, the lateral bore configured to receive a fastener therethrough to secure the lateral portion to the bone, the lateral portion contoured to engage a lateral portion of a femur;
a medial portion connected to the lateral portion, the medial portion engageable with the bone and including a medial bore extending through the medial portion, the medial bore configured to receive a fastener therethrough to secure the lateral portion to the bone, the medial portion contoured to engage a medial portion of a femur; and
a hinge connected to the lateral portion and the medial portion to allow relative movement of the lateral portion and the medial portion before the lateral portion and the medial portion are secured to the bone; and
a registration device connected to the plate and configured to interface with the surgical robot for registration of the plate and the bone.

2. The device of claim 1, wherein the hinge is a pivoting hinge configured to allow the lateral portion to rotate with respect to the medial portion.

3. The device of claim 1, wherein the hinge is a sliding hinge configured to allow the lateral portion to translate with respect to the medial portion.

4. The device of claim 3, wherein the sliding hinge includes a pair of pins connected to the lateral portion and the medial portion to engage the lateral portion and the medial portion to limit rotation of the lateral portion with respect to the medial portion.

5. The device of claim 4 wherein the sliding hinge includes an adjustment member connected to the lateral portion and the medial portion, the adjustment member operable to move the lateral portion with respect to the medial portion.

6. The device of claim 5, wherein the adjustment member is connected to the medial portion to form a socket joint and wherein the adjustment member forms a threaded engagement with the lateral portion.

7. The device of claim 6, wherein the hinge includes a pin detachably connected to the medial portion and engaged with an outer surface of the adjustment member to retain the adjustment member in the socket joint.

8. The device of claim 3, wherein the lateral portion includes a channel and wherein the medial portion includes a slider block located within the channel and translatable within the channel such that the channel guides translation of the slider block.

9. The device of claim 8, wherein the plate includes:
a first pin and a second pin connected to the slider block and at least partially located in a first guide channel and a second guide channel of the lateral portion, respectively; and
a third pin and a fourth pin connected to the lateral portion and at least partially located in a third guide channel and a fourth guide channel of the medial portion, respectively.

10. The device of claim 1, wherein the plate include a bone engagement surface configured to engage an external bone surface.

11. The device of claim 10, wherein the bone engagement surface includes a projection engageable with the external bone surface to increase friction therebetween.

12. The device of claim 1, wherein the lateral portion or the medial portion includes a boss extending from an outer portion of the lateral portion or the medial portion, the boss defining a bore configured to receive a distal portion of the registration device therein.

13. A method of registering a bone for a robotic knee arthroplasty using a surgical robot, the method comprising:
engaging a bone with a lateral portion of a plate, the lateral portion contoured to engage a lateral portion of the bone, the lateral portion including a lateral bore extending through the lateral portion;
fastening the lateral portion to the bone through the lateral bore;
adjusting a medial portion of the plate using a hinge of the plate connected to the lateral portion of the plate and configured to allow relative movement of the lateral portion and the medial portion before the lateral portion and the medial portion are secured to the bone, the medial portion contoured to engage a medial portion of the bone, the medial portion including a medial bore extending therethrough;
fastening the medial portion to the bone through the medial bore; and
registering the bone and the plate using the surgical robot and a registration device secured to the plate.

14. The method of claim 13, wherein adjusting the medial portion of the plate using the hinge includes rotating the medial portion of the plate with respect to the lateral portion of the plate using the hinge.

15. The method of claim 13, wherein adjusting the medial portion of the plate using the hinge includes translating the medial portion of the plate with respect to the lateral portion of the plate using the hinge.

16. The method of claim 13, wherein registering the bone includes optically imaging reference points of the registration device using an optical navigation system associated with the surgical robot.

17. The method of claim 13, further comprising:
removing the registration device from the plate; and
securing the registration device to the plate.

18. The method of claim 13, further comprising:
engaging the bone with the medial portion of the plate.

* * * * *